US008283446B2

(12) United States Patent
Jakobsen et al.

(10) Patent No.: US 8,283,446 B2
(45) Date of Patent: Oct. 9, 2012

(54) T CELL RECEPTOR MUTANTS

(75) Inventors: Bent Karsten Jakobsen, Oxon (GB); Nathaniel Ross Liddy, Oxon (GB)

(73) Assignee: Immunocore Limited, Oxon (GB)

( * ) Notice: Subject to any disclaimer, the term of this patent is extended or adjusted under 35 U.S.C. 154(b) by 91 days.

(21) Appl. No.: 12/850,425

(22) Filed: Aug. 4, 2010

(65) Prior Publication Data

US 2012/0027739 A1 Feb. 2, 2012

Related U.S. Application Data

(63) Continuation of application No. PCT/GB2010/001433, filed on Jul. 28, 2010.

(51) Int. Cl.

| | |
|---|---|
| ***C07K 1/00*** | (2006.01) |
| ***C07K 14/00*** | (2006.01) |
| ***C07K 17/00*** | (2006.01) |

(52) U.S. Cl. ....................................................... 530/350

(58) Field of Classification Search ........................ None
See application file for complete search history.

(56) References Cited

U.S. PATENT DOCUMENTS 7,915,036 B2 * 3/2011 Morgan et al. ............. 435/320.1

OTHER PUBLICATIONS

Paul WE, Fundamental Immunology, $3^{rd}$ ed., pp. 292-295, Raven Press, NY, 1993.*
Rudikoff S. et al. PNAS 79:1979-1983, 1982.*
Colman PM, Research in Immunology 145(1):33-36, 1994.*

* cited by examiner

*Primary Examiner* — Robert Landsman
(74) *Attorney, Agent, or Firm* — Vedder Price P.C.; Thomas J. Kowalski; Smitha B. Uthaman

(57) ABSTRACT

A T cell receptor (TCR) having the property of binding to EVDPIGHLY HLA-A1 complex and comprising a specified wild type TCR which has specific mutations in the TCR alpha variable domain and/or the TCR beta variable domain to increase affinity. Such TCRs are useful for adoptive therapy.

5 Claims, 11 Drawing Sheets

**Figure 1A. Wild Type MAGE-A3-specific TCR TRAV21*01/TRAJ28/TRAC alpha chain amino acid sequence (SEQ ID No: 2)**

```
                 10         20         30         40
                  *          *          *          *
KQEVTQIPAALSVPEGENLVLNCSFTDSAIYNLQWFRQDP
                 50         60         70         80
                  *          *          *          *
GKGLTSLLLIQSSQREQTSGRLNASLDKSSGRSTLYIAAS
                 90        100        110        120
                  *          *          *          *
QPGDSATYLCAVRPGGAGSYQLTFGKGTKLSVIPNIQNPD
                130        140        150        160
                  *          *          *          *
PAVYQLRDSKSSDKSVCLFTDFDSQTNVSQSKDSDVYITD
                170        180        190        200
                  *          *          *          *
KTVLDMRSMDFKSNSAVAWSNKSDFACANAFNNSIIPEDT

FFPSPESS
```

Figure 1B. Reference TCR alpha chain (see Figure 1C) DNA sequence (SEQ ID No: 4) (introduced cysteine is bold)

catatgaaaca agaagttactcaaattcctgcagctctga gtgtcccaga aggagaa aactgg ttctcaactgcagtt
tcactg atagcgctatttacaacctcc agtggtttaggca ggaccctggg aaaggtctcacatctctgttgctt attcagtc
a agtca gagagag caaacaagtgga agacttaatgcctcgctggataaa tcatcaggacgtagtactttatacattgc
agcttctcagcctggtg actcagcca cctacctctg tgctgtgaggccggg agggg ctg ggagtta ccaa ctcactttc
gggaagg ggaccaaactctcggt catac caaata tcca gaaccctgaccctg ccgtgtaccagctga gagactcta
agtcgagtgaca agtctg tctgcctattcaccg atttgattctcaaacaaat gtgtcacaaagta aggattctgatgtg ta
tatcacagaca aatgtgtgctag acatg aggtct atggacttcaaga gcaacagtgctgtggcctggag caacaaat
ctgactttgcatg tgcaaa cgccttcaa caaca gcatta ttcca gaagacaccttcttccccag cccagaaagttcctaa
gctt

Figure 1C. Reference TCR alpha chain – Wild type MAGE-A3-specific TCR TRAV21*01/TRAJ28/TRAC alpha chain amino acid sequence, but with cysteine (bold and underlined) substituted for T162 (i.e. T48 of the TRAC constant region) (SEQ ID No: 6)

```
                 10                  20                  30                  40
                  *                   *                   *                   *
K Q E V T Q I P A A L S V P E G E N L V L N C S F T D S A I Y N L Q W F R Q D P
                 50                  60                  70                  80
                  *                   *                   *                   *
G K G L T S L L L I Q S S Q R E Q T S G R L N A S L D K S S G R S T L Y I A A S
                 90                 100                 110                 120
                  *                   *                   *                   *
Q P G D S A T Y L C A V R P G G A G S Y Q L T F G K G T K L S V I P N I Q N P D
                130                 140                 150                 160
                  *                   *                   *                   *
P A V Y Q L R D S K S S D K S V C L F T D F D S Q T N V S Q S K D S D V Y I T D
                170                 180                 190                 200
                  *                   *                   *                   *
K C V L D M R S M D F K S N S A V A W S N K S D F A C A N A F N N S I I P E D T

F F P S P E S S
```

Figure 2A. Wild Type MAGE-A3-specific TCR TRBV5-1*01/TRBD1/TRBJ2-7*01/TRBC2 beta chain amino acid sequence (SEQ ID No: 3)

```
                 10                  20                  30
                  *                   *                   *
K A G V T Q T P R Y L I K T R G Q Q V T L S C S P I S G H R S V S W Y Q Q T P
40                  50                  60                  70
*                   *                   *                   *
G Q G L Q F L F E Y F S E T Q R N K G N F P G R F S G R Q F S N S R S E M N V
  80                  90                 100                 110
  *                   *                   *                   *
S T L E L G D S A L Y L C A S S P N M A D E Q Y F G P G T R L T V T E D L K N V
 120                 130                 140                 150
  *                   *                   *                   *
F P P E V A V F E P S E A E I S H T Q K A T L V C L A T G F Y P D H V E L S W W
 160                 170                 180                 190
  *                   *                   *                   *
V N G K E V H S G V S T D P Q P L K E Q P A L N D S R Y C L S S R L R V S A T
    200                 210                 220                 230
     *                   *                   *                   *
F W Q N P R N H F R C Q V Q F Y G L S E N D E W T Q D R A K P V T Q I V S A E
      240
       *
A W G R A D
```

Figure 2B Reference TCR beta chain (see figure 2C) DNA sequence (SEQ ID No: 5) (introduced cysteine is bold):

catatgaaagctggagttactcaaactccaagatatctgatcaaaacgagaggacagcaagtgacactgagctgct
cccctatctctgggcataggagtgtatcctggtaccaacagaccccaggacagggccttcagttcctctttgaatacttc
agtgagacacagagaaacaaaggaaacttccctggtcgattctcagggcgccagttctctaactctcgctctgagatg
aatgtgagcaccttggagctgggggactcggccctttatctttgcgccagcagcccgaacatggccgacgagcagta
cttcgggccgggcaccaggctcacggtcacagaggacctgaaaaacgtgttcccacccgaggtcgctgtgtttgagc
catcagaagcagagatctcccacacccaaaaggccacactggtgtgcctggccaccggtttctaccccgaccacgt
ggagctgagctggtgggtgaatgggaaggaggtgcacagtggggtctgcacagacccgcagcccctcaaggagc
agcccgccctcaatgactccagatacgctctgagcagccgcctgagggtctcggccaccttctggcaggacccccgc
aaccacttccgctgtcaagtccagttctacgggctctcggagaatgacgagtggacccaggatagggccaaacccgt
cacccagatcgtcagcgccgaggcctggggtagagcagactaagctt

Figure 2C. Reference TCR beta chain – Wild type MAGE-A3-specific TCR TRBV5-1*01/TRBD1/TRBJ2-7*01/TRBC2 beta chain amino acid sequence, but with cysteine (bold and underlined) substituted for S169 (i.e. S57 of the TRBC2 constant region) and with A187 substituted for C187 and D201 substituted for N201 (SEQ ID No: 7)

```
                10                  20                  30
                 *                   *                   *
KAGVTQTPRYLIKTRGQQVTLSCSPISGHRSVSWYQQTP
40                50                  60                  70
*                 *                   *                   *
GQGLQFLFEYFSETQRNKGNFPGRFSGRQFSNSRSEMNV
  80                90                  100                 110
  *                 *                   *                   *
STLELGDSALYLCASSPNMADEQYFGPGTRLTVTEDLKNV
 120                130                 140                 150
 *                   *                   *                   *
FPPEVAVFEPSEAEISHTQKATLVCLATGFYPDHVELSWW
 160                 170                 180                 190
 *                   *                   *                   *
VNGKEVHSGVCTDPQPLKEQPALNDSRYALSSRLRVSAT
    200                 210                 220                 230
    *                   *                   *                   *
FWQDPRNHFRCQVQFYGLSENDEWTQDRAKPVTQIVSAE
      240
      *
AWGRAD
```

FIGURE 3A

High Affinity MAGE-A3-specific TCR alpha chain variable domain amino acid sequence (SEQ ID No: 8):

KQEVTQIPAALSVPEGENLVLNCSFTDSAIYNLQWFRQDPGKGLTSLLLVRPYQRE
QTSGRLNASLDKSSGRSTLYIAASQPGDSATYLCAVRPGGAGSYQLTFGKGTKLSV
IP

FIGURE 3B

High Affinity MAGE-A3-specific TCR alpha chain variable domain amino acid sequence (SEQ ID No: 9):

KQEVTQIPAALSVPEGENLVLNCSFTDSAIYNLQWFRQDPGKGLTSLLLVRPSQRE
QTSGRLNASLDKSSGRSTLYIAASQPGDSATYLCAVRPGGAGSYQLTFGKGTKLSV
IP

FIGURE 4A

High Affinity MAGE-A3-specific TCR beta chain variable domain amino acid sequence (SEQ ID No: 10):

KAGVTQTPRYLIKTRGQQVTLSCSPISGHRSVSWYQQTPGQGLQFLFEYTDMTLR
NKGNFPGRFSGRQFSNSRSEMNVSTLELGDSALYLCASSPNMADEQYFGPGTRLT
VT

FIGURE 4B

High Affinity MAGE-A3-specific TCR beta chain variable domain amino acid sequence (SEQ ID No: 11):

KAGVTQTPRYLIKTRGQQVTLSCSPISGHRSVSWYQQTPGQGLQFLFEYFDMLLR
NKGNFPGRFSGRQFSNSRSEMNVSTLELGDSALYLCASSPNMADEQYFGPGTRLT
VT

FIGURE 5A

Wild Type MAGE-specific TCR WT alpha chain-2A-WT beta chain DNA sequence with Porcine teschovirus-1 2A sequence (bold and underlined) (SEQ ID No: 12):

gctagccgccaccatggaaaccctgctgggcctgctgatcctgtggctgcagctgcagtgggtctcttcgaagcagg
aagtgacccagatccctgccgccctgagcgtgcccgagggcgagaacctggtgctgaactgcagcttcaccgacag
cgccatctacaacctgcagtggttccggcaggaccccggcaagggcctgaccagcctgctgctgatccagagcagc
cagcgggagcagaccagcggcagactgaacgccagcctggacaagagcagcggcagaagcaccctgtatatcg
ccgccagccagcccggcgactccgccacctacctgtgcgctgtgcggcctggcggagccggcagctaccagctga
ccttcggcaagggcaccaagctgtccgtgatccccaatattcagaaccccgaccccgccgtgtaccagctgcggga
cagcaagtccagcgacaagagcgtgtgcctgttcaccgacttcgacagccagaccaacgtgtcccagagcaagga
cagcgacgtgtacatcaccgacaagaccgtgctggacatgcggagcatggacttcaagagcaacagcgccgtggc
ctggtccaacaagagcgacttcgcctgcgccaacgccttcaacaacagcatcatccccgaggacacctttttcccag
ccccgagagcagctgcgacgtcaaactggtggagaagtccttcgagacagacaccaacctgaacttccagaacct
gagcgtgatcggcttcagaattctgctgctgaaggtggccggcttcaacctgctgatgaccctgcggctgtggagcagc
ggctcccgggccaagagaagcggatccggcgccaccaacttttccctgctgaagcaggctggagatgtggag
gaaaaccctggccctaggatgggcagcagactgctgtgctgggtgctgctgtgtctgctgggagccggccctgtga
aggccggcgtgacccagacccccagatacctgatcaagacccagaggccagcaggtgacactgagctgcagcccc
atcagcggccacagaagcgtgtcctggtatcagcagacccccggacagggcctgcagttcctgttcgagtacttcag
cgagacacagcggaacaagggcaacttccccggcagattcagcggcaggcagttcagcaacagccgcagcgag
atgaacgtgtccaccctggaactgggcgacagcgccctgtacctgtgtgccagcagccccaacatggccgacgagc
agtacttcggccctggcacccggctgacggtaaccgaggacctgaagaacgtgttcccccccgaggtggccgtgttc
gagcccagcgaggccgagatcagccacacccagaaagccaccctggtgtgcctggccaccggcttctaccccgac
cacgtggagctgtcttggtgggtgaacggcaaagaggtgcacagcggagtctccaccgacccccagcccctgaaa
gagcagcccgccctgaacgacagccggtactgcctgagcagcagactgcgggtgtccgccaccttctggcagaac
cctagaaaccacttccggtgccaggtgcagttctacggcctgagcgagaacgacgagtggacccaggacagagcc
aagcccgtgacacagatcgtgtccgccgaggcctgggggcgcgccgattgcggcttcacaagcgagagctatcag
cagggcgtgctgtctgccaccatcctgtacgagatcctgctgggcaaggccaccctgtacgccgtgctggtgtccgcc
ctggtgctgatggccatggtgaagcggaaggacagccggggctaagtcgac

FIGURE 5B

Wild Type MAGE-specific TCR WT alpha chain-2A-WT beta chain amino acid sequence with Porcine teschovirus-1 2A sequence (bold and underlined) (SEQ ID No: 13)

```
            10             20             30             40
             *              *              *              *
M E T L L G L L I L W L Q L Q W V S S K Q E V T Q I P A A L S V P E G E N L V L
            50             60             70             80
             *              *              *              *
N C S F T D S A I Y N L Q W F R Q D P G K G L T S L L L I Q S S Q R E Q T S G R
            90            100            110            120
             *              *              *              *
L N A S L D K S S G R S T L Y I A A S Q P G D S A T Y L C A V R P G G A G S Y Q
           130            140            150            160
             *              *              *              *
L T F G K G T K L S V I P N I Q N P D P A V Y Q L R D S K S S D K S V C L F T D
           170            180            190
             *              *              *
F D S Q T N V S Q S K D S D V Y I T D K T V L D M R S M D F K S N S A V A W S
200            210            220            230            240
 *              *              *              *              *
N K S D F A C A N A F N N S I I P E D T F F P S P E S S C D V K L V E K S F E T D
           250            260            270            280
             *              *              *              *
T N L N F Q N L S V I G F R I L L L K V A G F N L L M T L R L W S S G S R A K R S
           290            300            310            320
             *              *              *              *
G S G **A T N F S L L K Q A G D V E E N P G P** R M G S R L L C W V L L C L L G A
           330            340            350
             *              *              *
G P V K A G V T Q T P R Y L I K T R G Q Q V T L S C S P I S G H R S V S W Y Q
360            370            380            390
 *              *              *              *
Q T P G Q G L Q F L F E Y F S E T Q R N K G N F P G R F S G R Q F S N S R S E
```

```
 400                410                420                430
  *                  *                  *                  *
MNVSTLELGDSALYLCASSPNMADEQYFGPGTRLTVTEDL
 440                450                460                470
  *                  *                  *                  *
KNVFPPEVAVFEPSEAEISHTQKATLVCLATGFYPDHVEL
480                 490                500                510
  *                  *                  *                  *
SWWVNGKEVHSGVSTDPQPLKEQPALNDSRYCLSSRLRV
   520                530                540                550
    *                  *                  *                  *
SATFWQNPRNHFRCQVQFYGLSENDEWTQDRAKPVTQIV
     560                570                580                590
      *                  *                  *                  *
SAEAWGRADCGFTSESYQQGVLSATILYEILLGKATLYAV
     600                610
      *                  *
LVSALVLMAMVKRKDSRG
```

FIG. 5B, cont.

Increased activation of MAGE-A3 improved-affinity TCR-transduced T cells in response to tumour cell lines.

Increased cytotoxicity of MAGE-A3 improved-affinity TCR-transduced T cells in response to a tumour cell line than wild type

T CELL RECEPTOR MUTANTS

This application claims the benefit of and incorporates by reference PCT/GB2010/001433 filed on 28 Jul. 2010.

This application incorporates by reference the contents of a 23.4 kb text file created on Aug. 4, 2010 and named "sequence_listing.txt," which is the sequence listing for this application.

The present invention relates to T cell receptors (TCRs) which bind the EVDPIGHLY (SEQ ID NO: 1) peptide (derived from the MAGE-3 protein) presented as apeptide-HLA-A1 complex, the TCRs being mutated relative to the native MAGE-A3 TCR alpha and/or beta variable domains and having binding affinities for, and/or binding half-lives for, the complex at least double that of a reference MAGE-A3 TCR.

BACKGROUND TO THE INVENTION

The EVDPIGHLY (SEQ ID No: 1) peptide corresponds to amino acid residue numbers 168-176 of the known MAGE-3 protein. The MAGE-3 protein is expressed in many tumour types, including melanomas, and other solid tumours such as Head and Neck Squamous Cell, lung, bladder, gastric and esophageal carcimomas. The MAGE-3 peptide EVDPIGHLY (SEQ ID No: 1) is the best characterised MAGE-3 epitope. It is recognised by both HLA-A1 and HLA-B35 restricted T cells. It is able to elicit cytotoxic activity against peptide-pulsed, HLA-A1 positive target cells, and MAGE-3-expressing HLA-A1 positive melanoma cell lines. The peptide, used as a vaccine, has been shown to induce tumour regression and elicit CTL responses in some of those patients.

Therefore, the EVDPIGHLY (SEQ ID NO: 1) HLA-A1 complex provides a cancer marker that the TCRs of the invention can target. For example, TCRs of the invention may be transformed into T-cells, rendering them capable of destroying tumour cells presenting that HLA complex, for administration to a patient in the treatment process known as adoptive therapy. For this purpose it would be desirable if the TCRs had a higher affinity and/or a slower off-rate for the peptide-HLA complex than native TCRs specific for that complex. Dramatic increases in affinity have been associated with a loss of antigen specificity in TCR gene-modified CD8 T cells, which could result in the nonspecific activation of these TCR-transfected CD8 T cells, so TCRs having somewhat a higher affinity and/or a slower off-rate for the peptide-HLA complex than native TCRs specific for that complex, but not a dramatically higher affinity and/or dramatically slower off-rate for the peptide-HLA than native TCRs, would be preferred for adoptive therapy (see Zhao et al., (2007) *J. Immunol.* 179: 5845-54; Robbins et al., (2008) *J. Immunol.* 180: 6116-31; and see also published WO 2008/038002).

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR Vβ region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The α and β chains of αβ TCR's are generally regarded as each having two "domains", namely variable and constant domains. The variable domain consists of a concatenation of variable region and joining region. In the present specification and claims, the term "TCR alpha variable domain" therefore refers to the concatenation of TRAV and TRAJ regions, and the term TCR alpha constant domain refers to the extracellular TRAC region, or to a C-terminal truncated TRAC sequence. Likewise the term "TCR beta variable domain" refers to the concatenation of TRBV and TRBD/TRBJ regions, and the term TCR beta constant domain refers to the extracellular TRBC region, or to a C-terminal truncated TRBC sequence.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

We have confirmed that a native MAGE-3 TCR (Clone EB81-103 from Dr. Pierre G. Coulie, Cellular Genetics Unit, University of Louvain, Avenue Hippocrate 74, UCL 7459, B-1200 Brussels, Belgium; see also Karanikas, et. al. (2003) "Monoclonal anti-MAGE-3 CTL responses in melanoma patients displaying tumor regression after vaccination with a recombinant canarypox virus." *J. Immunol.* 171(9): 4898-904)) has the following alpha chain and beta chain V, J and C gene usage:

Alpha chain—TRAV21*01/TRAJ28/TRAC (the extracellular sequence of the native MAGE-A3 TCR alpha chain is given in SEQ ID No: 2)

Beta chain:—TRBV5-1*01/TRBD1/TRBJ2-7*01/TRBC2 (the extracellular sequence of the native MAGE-A3 TCR beta chain is given in SEQ ID No: 3). (Note that the TRBV5-1 sequence has 2 allelic variants, designated in IMGT nomenclature as TRBV5-1*01 and *02 respectively, and the native MAGE-A3 TCR clone referred to above has the *01 variation. In the same way, the TRBJ2-7 sequence has two known variations and it is the *01 sequence which is present in the TCR clone referred to above. Note also that the absence of a"*" qualifier means that only one allele is known for the relevant sequence.)

The terms "wild type TCR", "native TCR", "wild type MAGE-A3 TCR" and "native MAGE-A3 TCR" are used synonymously herein to refer to this naturally occurring TCR having the extracellular alpha and beta chain SEQ ID Nos: 2 and 3.

DETAILED DESCRIPTION OF THE INVENTION

According to the invention, there is provided a T cell receptor (TCR) having the property of binding to EVDPIGHLY (SEQ ID No: 1) HLA-A1 complex and comprising a TCR alpha variable domain and a TCR beta variable domain, characterized in that:

the TCR alpha variable domain has the amino acid sequence from K1 to P114 of SEQ ID No: 2 except that at least one of the following mutations is present, namely 50I is mutated to 50V;

51Q is mutated to 51R;

52S is mutated to 52P;

53S is mutated to 53Y; and/or the TCR beta variable domain has the amino acid sequence from K1 to T112 of SEQ ID No: 3 except that at least one of the following mutations is present, namely 50F is mutated to 50T;

51S is mutated to 51D;

52E is mutated to 52M;

53T is mutated to 53L;

54Q is mutated to 54L.

TCRs of the invention preferably have a binding affinity for, and/or a binding half-life for, the EVDPIGHLY(SEQ ID NO: 1) -HLA-A1 complex at least double that of a reference MAGE-A3 TCR, the said reference MAGE-A3 TCR having the extracellular alpha chain sequence SEQ ID No: 6 and the extracellular beta chain sequence SEQ ID No: 7.

Note that SEQ ID No: 6 is the native alpha chain extracellular sequence ID No:2 except that C162 has been substituted for T162 (i.e. T48 of TRAC). Likewise SEQ ID No: 7 is the native beta chain extracellular sequence ID No: 3 except that C169 has been substituted for S169 (i.e. S57 of TRBC2), A187 has been substituted for C187 and D201 has been substituted for N201. These cysteine substitutions relative to the native alpha and beta chain extracellular sequences enable the formation of an interchain disulfide bond which stabilises the refolded soluble TCR, ie the TCR formed by refolding extracellular alpha and beta chains. Use of the stable disulfide linked soluble TCR as the reference TCR enables more convenient assessment of binding affinity and binding half life. The other mutations in the alpha chain SEQ ID No: 6 and the beta chain SEQ ID No: 7 relative to the native alpha and beta chains SEQ ID Nos: 2 and 3 are "silent" in the sense that they do not affect the binding affinity or binding half life relative the native sequence. Hence, Hence, if a TCR of the invention has a binding affinity for, and/or a binding half-life for, the EVDPIGHLY(SEQ ID NO: 1) -HLA-A1 complex at least double that of the reference MAGE-A3 TCR, it impliedly also meets those criteria with respect to the native MAGE-A3 TCR clone referred to above.

The "reference MAGE-A3 TCR having the extracellular alpha chain sequence SEQ ID No: 6 and the extracellular beta chain sequence SEQ ID No: 7" is referred to synonymously hereafter either as "the reference TCR" or "the reference MAGE-A3 TCR".

Binding affinity (inversely proportional to the equilibrium constant $K_D$) and binding half-life (expressed as $T_{1/2}$)) can be determined by any appropriate method. It will be appreciated that doubling the affinity of a TCR results in halving the $K_D$. $T_{1/2}$ is calculated as ln2 divided by the off-rate ($_{koff}$). So doubling of $T_{1/2}$ results in a halving in $k_{off}$ $K_D$ and $k_{off}$ values for TCRs are usually measured for soluble forms of the TCR, i.e. those forms which are truncated to remove hydrophobic transmembrane domain residues. Therefore it is to be understood that a given TCR meets the requirement that it has a binding affinity for, and/or a binding half-life for, the EVDPIGHLY(SEQ ID NO: 1) -HLA-A1 complex if a soluble form of that TCR meets that requirement. Preferably the binding affinity or binding half-life of a given TCR is measured several times, for example 3 or more times, using the same assay protocol, and an average of the results is taken. In a preferred embodiment these measurements are made using the Surface Plasmon Resonance (BIAcore) method of Example 3 herein. The reference MAGE-A3 TCR has a $K_D$ of approximately 250 μM as measured by that method, and the $k_{off}$ was approximately 0.2 s−1 (i.e $T_{1/2}$, was approximately 3 s).

The TCRs of the invention have an affinity and/or a binding half-life for the EVDPIGHLY(SEQ ID NO: 1) HLA-A1 complex at least twice that of the reference MAGE-A3 TCR, while retaining acceptable EVDPIGHLY(SEQ ID NO: 1) HLA-A1 complex specificity, for example similar to the reference MAGE A3 TCR. TCRs required for transfection of T-cells for adoptive therapy should have somewhat higher affinities and/or longer binding half-lives for the said EVDPIGHLY(SEQ ID NO: 1) HLA-A1 complex than the reference MAGE-A3 TCR (though still respectively at least twice those of the native TCR).

For example, TCRs of the invention may have a $K_D$ for the complex of from about 6 μM to about 70 μM and/or have a binding half-life (T½) for the complex of from about 1 to about 11 s.

For the purposes of the present invention, a TCR is a moiety having at least one TCR alpha and/or TCR beta variable domain. Generally they comprise both a TCR alpha variable domain and a TCR beta variable domain. They may be αβ heterodimers or may be single chain format. For use in adoptive therapy, an αβ heterodimeric TCR may, for example, be transfected as full length chains having both cytoplasmic and transmembrane domains. If desired, an introduced disulfide bond between residues of the respective constant domains may be present (see for example WO 2006/000830).

Whatever the format, the TCRs of the invention are mutated relative to the native MAGE-A3 TCR having the extracellular alpha and beta chain sequences SEQ ID Nos: 2 and 3 in their alpha variable domain (extending from K1 to P114 of SEQ ID No: 2) and/or beta variable domain (extending from K1 to T112 of SEQ ID No: 3).

The native MAGE-A3 or the reference MAGE-A3 TCR can be used as a template into which the various mutations that cause high affinity and/or a slow off-rate for the interaction between TCRs of the invention and the EVDPIGHLY (SEQ ID NO: 1) HLA-A1 complex can be introduced. Embodiments of the inventions include TCRs which are mutated relative to the □ chain variable domain extending from K1 to P114 of SEQ ID No: 2 and/or □ chain variable domain extending from K1 to T112 of SEQ ID No: 3 in at least one complementarity determining region (CDR) and/or variable domain framework region thereof.

Mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see Sambrook & Russell, (2001) Molecular Cloning—A Laboratory Manual ($3^{rd}$ Ed.) CSHL Press. Further information on LIC procedures can be found in (Rashtchian, (1995) *Curr Opin Biotechnol* 6 (1): 30-6).

One method for generating high affinity MAGE-3 TCRs of the invention is selection from a diverse library of phage particles displaying such TCRs as disclosed in WO 2004/044004.

It should be noted that any αβ TCR that comprises similar Vα and Vβ gene usage and therefore variable domain amino acid sequences to that of the native MAGE-A3 TCR or reference MAGE-3 TCR could make a convenient template TCR. It would then be possible to introduce into the DNA encoding one or both of the variable domains of the template αβ TCR the changes required to produce the mutated TCRs of the invention. As will be obvious to those skilled in the art, the necessary mutations could be introduced by a number of methods, for example site-directed mutagenesis.

In some embodiments, the TCRs of the invention have the alpha chain variable domain extending from K1 to P114 of SEQ ID No: 2, except that amino acid residues at one or more of positions 50I, 51Q, 52S or 53S are mutated, and/or having the beta chain variable domain extending from K1 to T112 of SEQ ID No: 3, except that amino acid residues at one or more of positions 50F, 51S, 52E, 53T or 54Q are mutated. For example, TCRs of the invention may have one or more of alpha chain variable domain amino acid residues 50V, 51R, 52P or 53Y using the numbering shown in SEQ ID No: 2, and/or one or more of beta chain variable domain amino acid residues 50T, 51D, 52M, 53L, or 54L using the numbering shown in SEQ ID No: 3.

Specific TCRs of the invention include those comprising one of the alpha chain variable domain amino acid sequences SEQ ID Nos: 8 and 9 and/or one of the beta chain variable domain amino acid sequences SEQ ID Nos: 10 and 11. Thus TCRs with the variable domain sequence of the wild type alpha chain (K1 to P114 of SEQ ID No: 2) may be associated with a beta chain having one of SEQ ID Nos: 10 and 11. Alternatively, an alpha chain having one of SEQ ID Nos: 8 and 9 may be associated with the variable domain sequence of the wild type beta chain (K1 to T112 of SEQ ID No: 3). Alternatively an alpha chain having one of SEQ ID Nos: 8 and 9 may be associated with a beta chain having one of SEQ ID Nos: 10 and 11.

Phenotypically silent variants of the TCRs discussed above also form part of this invention. The term "phenotypically silent variants" refers to TCRs which are identical in sequence to a TCR of the invention except that they incorporate changes in the constant and/or variable domains which do not alter the affinity and/or off-rate for the interaction with the peptide-HLA complex. One example of such a variant is provided by TCRs of the invention in which the TCR alpha constant domain contains a Phenylalanine (F) amino acid residue substituted for the 135 Serine (S) amino acid residue using the numbering of SEQ ID No: 2.

As mentioned above, αβ heterodimeric TCRs of the invention may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned in the preceding paragraph, αβ heterodimeric TCRs of the invention may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

Since the αβ heterodimeric TCRs of the invention have utility in adoptive therapy, the invention includes an isolated cell, especially a T-cell, presenting a TCR of the invention. There are a number of methods suitable for the transfection of T cells with DNA or RNA encoding the TCRs of the invention. (See for example Robbins et al., (2008) *J. Immunol.* 180: 6116-6131)). T cells expressing the TCRs of the invention will be suitable for use in adoptive therapy-based treatment of MAGE-$3^+$ HLA-$A1^+$ cancers. As will be known to those skilled in the art there are a number of suitable methods by which adoptive therapy can be carried out. (See for example Rosenberg et al., (2008) *Nat Rev Cancer* 8 (4): 299-308).

For use in adoptive therapy, the invention also includes cells harbouring a TCR expression vector which comprises nucleic acid encoding the TCR of the invention in a single open reading frame or two distinct open reading frames. Also included in the scope of the invention are cells harbouring a first expression vector which comprises nucleic acid encoding the alpha chain of a TCR of the invention, and a second expression vector which comprises nucleic acid encoding the beta chain of a TCR of the invention, The TCRs of the invention intended for use in adoptive therapy are glycosylated when expressed by the transfected T cells. As is well known, the glycosylation pattern of transfected TCRs may be modified by mutations of the transfected gene.

For administration to patients, T cells transfected with TCRs of the invention may be provided in pharmaceutical composition together with a pharmaceutically acceptable carrier. Cells in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by the intravenous route. Such compositions may be prepared by any method known in the art of pharmacy, for example by mixing the active ingredient with the carrier (s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

EXAMPLES

The invention is further described in the following examples in which the following Figures are referred to.

FIGS. 1A and 2A respectively show the extracellular amino acid sequences of the native MAGE-A3 TCR alpha chain having the TRAV21*01/TRAJ28/TRAC gene usage, and of the native MAGE-A3 TCR beta chain having the TRBV5-1*01/TRBD1/TRBJ2-7*01/TRBC2 gene usage (SEQ ID Nos: 2 and 3 respectively).

FIGS. 1B and 2B respectively show DNA sequences encoding soluble wild-type MAGE-A3 TCR alpha and beta chains also referred to as the reference MAGE-A3 TCR alpha and beta chains. These sequences include additional cysteine residues to form a non-native disulphide bond. The mutated codons encoding the additional cysteine residues are bold. The NdeI and HindIII restriction enzyme recognition sequences are underlined.

FIGS. 1C and 2C respectively show the soluble wild-type MAGE-A3 TCR, or reference MAGE-A3 TCR, alpha and beta chain extracellular amino acid sequences (SEQ ID Nos: 6 and 7 respectively) produced from the DNA sequences of FIGS. 1B and 2B respectively, but without the introduced leading methionine inserted for efficient expression in bacteria. The introduced cysteines are bold and underlined.

FIGS. 3A-B show the alpha chain variable domain amino acid sequences of MAGE-A3 TCR variants in accordance with the invention. The mutated residues are bold and underlined.

FIGS. 4A-B show the beta chain variable domain amino acid sequences of MAGE-A3 TCR variants in accordance with the invention. The mutated residues are bold and underlined.

FIG. 5A shows the DNA sequence for the wild type MAGE-A3-specific TCR gene (WT alpha chain-2A-WT beta chain construct with the Porcine teschovirus-1 2A sequence bold and underlined) for transduction of T-cells.

FIG. 5B shows the amino acid sequence of the wild type MAGE-A3-specific TCR for T-cell transduction produced from the DNA sequence of FIG. 5. The Porcine teschovirus-1 2A sequence is bold and underlined.

Example 1

Figure 6:
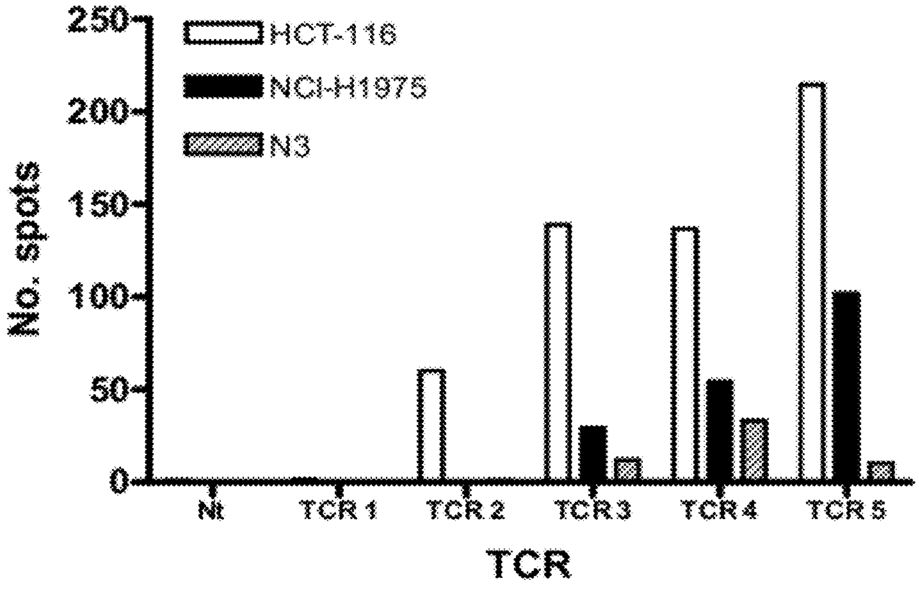
FIG. 6 shows the IFN-γ release of MAGE-A3 TCR-transduced T-cells in response to a range of target cells in an ELISPOT assay. These figures show the increased specific activation of T cells transduced with higher affinity MAGE-A3 TCRs compared to T cells transduced with the native MAGE-A3 TCR.

Cloning of the Reference MAGE-A3 TCR Alpha and Beta Chain Variable Region Sequences into pGMT7-Based Expression Plasmids The reference MAGE-A3 TCR variable alpha and TCR variable beta domains were PCR amplified from total cDNA isolated from a MAGE-3 T cell clone (Clone EB81-103 from Pierre Coulie University of Louvain, Belgium). In the case of the alpha chain, an alpha chain variable region sequence specific oligonucleotide A1 (ggaattccatatgaaacaagaagttactcaaattcc SEQ ID No: 14) which encodes the restriction site NdeI and an introduced methionine for efficient initiation of expression in bacteria, and an alpha chain constant region sequence specific oligonucleotide A2 (ttgtcagtcgacttagagtctctcagctggtacacg SEQ ID No: 15) which encodes the restriction site SalI are used to amplify the alpha chain variable region. In the case of the beta chain, a beta chain variable region sequence specific oligonucleotide B1 (gaattccatatgaaagctggagttactcaaactccaag SEQ ID No: 16) which encodes the restriction site NdeI and an introduced methionine for efficient initiation of expression in bacteria, and a beta chain constant region sequence specific oligonucleotide B2 (tagaaaccggtggccaggcacaccagtgtggc SEQ ID No: 17) which encodes the restriction site AgeI are used to amplify the beta chain variable region.

The alpha and beta variable regions were cloned into pGMT7-based expression plasmids containing either Cα or Cβ by standard methods described in Molecular Cloning a Laboratory Manual Third edition by Sambrook and Russell. Plasmids were sequenced using an Applied Biosystems 3730×1 DNA Analyzer.

The DNA sequences encoding the TCR alpha chain cut with NdeI and SalI were ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI.

Ligation

Ligated plasmids were transformed into competent *Escherichia coli* strain XL1-blue cells and plated out on LB/agar plates containing 100 μg/ml ampicillin. Following incubation overnight at 37° C., single colonies are picked and grown in 10 ml LB containing 100 μg/ml ampicillin overnight at 37° C. with shaking. Cloned plasmids were purified using a Miniprep kit (Qiagen) and the plasmids were sequenced using an Applied Biosystems 3730xl DNA Analyzer.

FIGS. 1C and 2C show respectively the soluble disulfide-linked reference MAGE-A3 TCR α and β chain extracellular amino acid sequences (SEQ ID Nos: 6 and 7 respectively) produced from the DNA sequences of FIGS. 1B and 2B respectively, but without the introduced leading methionine inserted for efficient expression in bacteria. Note that cysteines were substituted in the constant regions of the alpha and beta chains to provide an artificial inter-chain disulphide bond on refolding to form the heterodimeric TCR. The introduced cysteines are shown in bold and underlined. The restriction enzyme recognition sequences in the DNA sequences of FIGS. 1B and 2B are underlined.

Example 2

Expression, Refolding and Purification of Soluble Reference MAGE-A3 TCR

The expression plasmids containing the TCR α-chain and β-chain respectively, as prepared in Example 1, were transformed separately into *E. coli* strain Rosetta (DE3)pLysS, and single ampicillin-resistant colonies were grown at 37° C. in TYP (ampicillin 100 μg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA,) before being pelleted by centrifugation for 15 minutes at 4,000 rpm. Detergent and salt was then removed by a similar wash in the following buffer: 50 mM Tris-HCl pH 8.0, 1 mM NaEDTA, pH8.0. Finally, the inclusion bodies were divided into 30 mg aliquots and frozen at −70° C. Inclusion body protein yield was quantified by solubilising with 6 M Guanidine-HCl and an OD measurement was taken on a Hitachi U-2001 Spectrophotometer. The protein concentration was then calculated using the extinction coefficient.

Approximately 15 mg of TCR β chain and 15 mg of TCR α chain solubilised inclusion bodies were thawed from frozen stocks and diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in dialysis tubing cellulose membrane (Sigma-Aldrich; Product No. D9402) against 10 L $H_2O$ at 5° C.±3° C. for 18-20 hours.

After this time, the dialysis buffer was changed twice to fresh 10 mM Tris pH 8.1 (10 L) and dialysis was continued at 5° C.±3° C. for another ~8 hours.

Soluble TCR was separated from misfolded, degradation products and impurities by loading the dialysed refold onto a POROS 50HQ anion exchange column and eluting bound protein with a gradient of 0-500 mM NaCl in 10 mM Tris pH 8.1 over 6 column volumes using an Akta purifier (GE Healthcare). Peak fractions were then stored at 4° C. and analysed by Coomassie-stained SDS-PAGE before being pooled and concentrated. Finally, the soluble TCR was purified and characterised using a GE Healthcare Superdex 75HR gel filtration column pre-equilibrated in PBS buffer (Sigma). The peak eluting at a relative molecular weight of approximately 50 kDa was pooled and concentrated prior to characterisation by BIAcore surface plasmon resonance analysis.

Example 3

Binding Characterisation

BIAcore Analysis

A surface plasmon resonance biosensor (BIAcore 3000™) can be used to analyse the binding of a soluble TCR to its peptide-MHC ligand. This is facilitated by producing soluble biotinylated peptide-HLA ("pHLA") complexes which can be immobilised to a streptavidin-coated binding surface (sensor chip). The sensor chips comprise four individual flow cells which enable simultaneous measurement of T-cell receptor binding to four different pHLA complexes. Manual injection of pHLA complex allows the precise level of immobilised class I molecules to be manipulated easily.

Biotinylated class I HLA-A*01 molecules were refolded in vitro from bacterially-expressed inclusion bodies containing the constituent subunit proteins and synthetic peptide, followed by purification and in vitro enzymatic biotinylation (O'Callaghan et al. (1999) Anal. Biochem. 266: 9-15). HLA-A*01-heavy chain was expressed with a C-terminal biotinylation tag which replaces the transmembrane and cytoplasmic domains of the protein in an appropriate construct. Inclusion body expression levels of ~75 mg/litre bacterial culture were obtained. The MHC light-chain or β2-microglobulin (β2 m) was also expressed as inclusion bodies in *E. coli* from an appropriate construct, at a level of ~500 mg/litre bacterial culture.

*E. coli* cells were lysed and inclusion bodies were purified to approximately 80% purity. Synthetic peptide (MAGE-A3 EVDPIGHLY(SEQ ID NO: 1)) was dissolved in DMSO to a final concentration of 4mg/ml. Inclusion bodies of β2 m and heavy chain were denatured separately in 6 M guanidine-HCl, 50 mM Tris pH 8.1, 100 mM NaCl, 10 mM DTT, 10 mM EDTA. Refolding buffer was prepared containing 0.4 M L-Arginine, 100 mM Tris pH 8.1, 3.7 mM cystamine dihydrochloride, 6.6 mM cysteamine hydrochloride and chilled to <5° C. Preferably the peptide was added first to the refold buffer, followed by addition of denatured β2m then addition of denatured heavy chain. The MAGE-A3 EVDPIGHLY (SEQ ID NO: 1peptide was added to the refold buffer at 4 mg/litre (final concentration). Then 30 mg/litre β2 m followed by 30 mg/litre heavy chain (final concentrations) were added. Refolding was allowed to reach completion at 4 ° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient in 10 mM Tris pH 8.1 using an Akta purifier (GE Healthcare). HLA-A*01-peptide complex eluted at approximately 250 mM NaCl, and peak fractions were collected, a cocktail of protease inhibitors (Calbiochem) was added and the fractions were chilled on ice.

Biotinylation tagged pHLA molecules were buffer exchanged into 10 mM Tris pH 8.1, 5 mM NaCl using a GE Healthcare fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM $MgCl_2$, and 5 μg/ml BirA enzyme (purified according to O'Callaghan et al. (1999) *Anal. Biochem.* 266: 9-15). The mixture was then allowed to incubate at room temperature overnight.

The biotinylated pHLA-A*01 molecules were purified using gel filtration chromatography. A GE Healthcare Superdex 75 HR 10/30 column was pre-equilibrated with filtered PBS and 1 ml of the biotinylation reaction mixture was loaded and the column was developed with PBS at 0.5 ml/min using an Akta purifier (GE Healthcare). Biotinylated pHLA-A*01 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*01 molecules were stored frozen at −20° C.

Such immobilised complexes are capable of binding both T-cell receptors and the coreceptor CD8αα, both of which may be injected in the soluble phase. The pHLA binding properties of soluble TCRs are observed to be qualitatively and quantitatively similar if the TCR is used either in the soluble or immobilised phase. This is an important control for partial activity of soluble species and also suggests that biotinylated pHLA complexes are biologically as active as non-biotinylated complexes.

The BIAcore 3000™ surface plasmon resonance (SPR) biosensor measures changes in refractive index expressed in response units (RU) near a sensor surface within a small flow cell, a principle that can be used to detect receptor ligand interactions and to analyse their affinity and kinetic parameters. The BIAcore experiments were performed at a temperature of 25° C., using PBS buffer (Sigma, pH 7.1-7.5) as the running buffer and in preparing dilutions of protein samples. Streptavidin was immobilised to the flow cells by standard amine coupling methods. The pHLA complexes were immobilised via the biotin tag. The assay was then performed by passing soluble TCR over the surfaces of the different flow cells at a constant flow rate, measuring the SPR response in doing so.

Equilibrium Binding Constant

The above BIAcore analysis methods were used to determine equilibrium binding constants. Serial dilutions of the disulfide linked soluble heterodimeric form of the reference MAGE-A3 TCR were prepared and injected at constant flow rate of 5μl $min^{-1}$ over two different flow cells; one coated with ~1000 RU of specific EVDPIGHLY (SEQ ID NO: 1) HLA-A*01 complex, the second coated with ~1000 RU of non-specific HLA-A2 -peptide (KIFGSLAFL (SEQ ID No: 18)) complex. Response was normalised for each concentration using the measurement from the control cell. Normalised data response was plotted versus concentration of TCR sample and fitted to a non-linear curve fitting model in order to calculate the equilibrium binding constant, $K_D$. (Price &

Dwek, Principles and Problems in Physical Chemistry for Biochemists ($2^{nd}$ Edition) 1979, Clarendon Press, Oxford). The disulfide linked soluble form of the reference MAGE-A3 TCR (Example 2) demonstrated a $K_D$ of approximately 250 μM. From the same BIAcore data the T½ was approximately 3 s.

Kinetic Parameters

The above BIAcore analysis methods were also used to determine equilibrium binding constants and off-rates.

For TCRs (see Example 4 below) $K_D$ was determined by experimentally measuring the dissociation rate constant, $k_{off}$, and the association rate constant, $k_{on}$. The equilibrium constant $K_D$ was calculated as $k_{off}/k_{on}$.

TCR was injected over two different cells one coated with ~300 RU of specific EVDPIGHLY (SEQ ID NO: 1) HLA-A*01 complex, the second coated with ~300 RU of non-specific HLA-A1 -peptide complex. Flow rate was set at 50 μl/min. Typically 250 μl of TCR at a concentration equivalent to ~10 times the $K_D$ was injected. Buffer was then flowed over until the response had returned to baseline or >2 hours had elapsed. Kinetic parameters were calculated using BIAevaluation software. The dissociation phase was fitted to a single exponential decay equation enabling calculation of half-life.

Example 4

Generation of Variants of the Reference MAGE-A3 TCR

Phage display is one means by which libraries of MAGE-A3 TCR variants can be generated in order to identify higher affinity mutants. The TCR phage display and screening methods described in (Li et al, (2005) Nature Biotech 23 (3): 349-354) were applied to the MAGE-A3 TCR of Example 2.

TCRs with affinities and/or binding half-lives at least twice that of the reference MAGE-A3 TCR (and therefore impliedly at least twice that of the native TCR) were identified, having one or more of alpha chain variable domain amino acid residues 50V, 51R, 52P or 53Y using the numbering shown in SEQ ID No: 2 and/or one or more of beta chain variable domain amino acid residues 50T, 51D, 52M, 53L, or 54L using the numbering shown in SEQ ID No: 3.

Specific examples of the amino acid sequences of the variable regions of the alpha chains (SEQ ID Nos: 8 and 9) and beta chains (SEQ ID Nos: 10 and 11) of higher affinity TCRs are shown in FIGS. 3A-B and 4A-B respectively. These alpha chains are mutated in CDR2 and beta chains are mutated in CDR2.

TCR heterodimers were refolded using the method of Example 2 above (including the introduced cysteines in the constant regions to provide the artificial inter-chain disulphide bond). In that way TCRs were prepared, consisting of (a) the reference TCR beta chain, together with alpha chains which include the variable domains SEQ ID Nos: 8 and 9; (b) the reference TCR alpha chain, together with beta chains which include the beta chain variable domains SEQ ID Nos: 10 and 11; and (c) various combinations of beta and alpha chains including the mutant variable domains.

The interaction between these soluble disulfide-linked MAGE-A3 TCRs and the EVDPIGHLY(SEO ID NO: 1) HLA-A*01 complex was analysed using the BIAcore method described above, and the binding data is shown in Table 1.

TABLE 1

| TCR variable domain SEQ ID | | | | $k_{on}$ | |
|---|---|---|---|---|---|
| α | β | $k_{off}(s^{-1})$ | T½ | $(M^{-1}s^{-1})$ | $K_D$ |
| 8 | 3 | 0.114 | 6.1 sec | NM | 6.55 μM |
| 9 | 3 | 0.95 | <1 sec | 1.7e4 | 55 μM |
| 2 | 10 | 0.0666 | 10.4 sec | NM | 9.43 μM |
| 2 | 11 | 0.094 | 7.4 sec | 1.4e4 | 6.7 μM |

Example 5

Transfection of T-Cells with Variants of the Native MAGE-A3 TCR (a) Lentiviral Vector Preparation by Express-in-Mediated Transient Transfection of 293T Cells A $3^{rd}$ generation lentiviral packaging system is used to package lentiviral vectors containing the gene encoding the desired TCR. 293T cells are transfected with 4 plasmids (one lentiviral vector containing the TCR alpha chain-P2A-TCR beta chain single ORF gene described in Example 5c, and 3 plasmids containing the other components necessary to construct infective but non-replicative lentiviral particles) using Express-In-mediated transfection (Open Biosystems).

For transfection take one T150 flask of 293T cells in exponential growth phase, with cells evenly distributed on the plate, and slightly more than 50% confluent. Bring Express-In aliquots to room temperature. Place 3 ml Serum-Free Medium (RPMI 1640+10 mM HEPES) in a sterile 15 ml conical tube. Add 174 μl of Express-In Reagent directly into the Serum-Free Medium (this provides for a 3.6:1 weight ratio of Reagent to DNA). Mix thoroughly by inverting tubes 3-4 times and incubate at room temperature for 5-20 minutes.

In a separate 1.5 ml microtube, add 15 μg plasmid DNA to premixed packaging mix aliquots (containing 18 μg pRSV.REV (Rev expression plasmid), 18 μg pMDLg/p.RRE (Gag/Pol expression plasmid), 7 μg pVSV-G (VSV glycoprotein expression plasmid), usually ~22 μl, and pipette up and down to ensure homogeneity of the DNA mix. Add ~1 ml of Express-In/Serum-Free Medium to the DNA mix drop wise then pipette up and down gently before transferring back to the remainder of the Express-In/Serum-Free Medium. Invert tube 3-4 times and incubate at room temperature for 15-30 minutes.

Remove old culture medium from flask of cells. Add Express-In/medium/DNA (3 ml) complex to flask direct into the bottom of an upright flask of 293T cells. Slowly place flask flat to cover cells and very gently rock the flask to ensure even distribution. After 1 minute add 22 ml fresh culture medium ($R_{10}$+HEPES: RPMI 1640, 10% heat-inactivated FBS, 1% Pen/Strep/L-glutamine, 10 mM HEPES) and carefully return to incubator. Incubate overnight at 37° C./5% $CO_2$. After 24 hours, proceed to harvest the medium containing packaged lentiviral vectors.

To harvest the packaged lentiviral vectors, filter the cell culture supernatent through a 0.45 micron nylon syringe filter, centrifuge the culture medium at 10,000 g for 18 hours (or 112,000 g for 2 hours), remove most of the supernatant (taking care not to disturb the pellet) and resuspend the pellet in the remaining few ml of supernatant (usually about 2 ml from a 31 ml starting volume per tube). Snap freeze on dry ice in 1 ml aliquots and store at −80° C.

(b) Transduction of T Cells with Packaged Lentiviral Vectors Containing Gene of Interest Prior to transduction with the packaged lentiviral vectors, human T cells (CD8 or CD4 or both depending on requirements) are isolated from the blood of healthy volunteers. These cells are counted and incubated overnight in $R_{10}$ containing 50 U/ml IL-2 at $1\times10^6$ cells per ml (0.5 ml/well) in 48 well plates with pre-washed anti-CD3/CD28 antibody-coated microbeads (Dynal T cell expander, Invitrogen) at a ratio of 3 beads per cell.

After overnight stimulation, 0.5 ml of neat packaged lentiviral vector is added to the desired cells. Incubate at 37° C./5% $CO_2$ for 3 days. 3 days post-transduction count cells and dilute to $0.5\times10^6$ cells/ml. Add fresh medium containing IL-2 as required. Remove beads 5-7 days post-transduction. Count cells and replace or add fresh medium containing IL-2 at 2 day intervals. Keep cells between $0.5\times10^6$ and $1\times10^6$ cells/ml. Cells can be analysed by flow cytometry from day 3 and used for functional assays (e.g. ELISpot for IFNγ release) from day 5. From day 10, or when cells are slowing division and reduced in size, freeze cells in aliquots of at least $4\times10^6$ cells/vial (at $1\times10^7$ cells/ml in 90% FBS/10% DMSO) for storage.

(c) Wild Type (wt) TCR Gene for T-Cell Transfection by Methods (a) and (B) Above FIG. 5A is a DNA sequence (SEQ ID No: 12) encoding the native MAGE-A3 TCR (codon-optimised for maximal human cell expression). It is a full length alpha chain (TRAV21)-Porcine teschovirus-1 2A-full length beta chain (TRBV5-1) single open reading frame construct. The 2A sequence is underlined, and is preceded by nucleotides encoding a furin cleavage site to assist proteolytic removal of the 2A sequence (discussed further below in relation to FIG. 5B (SEQ ID No: 13). Peptide bond skipping during protein translation of the mRNA at the 3' end of the 2A sequence produces two proteins: 1) alpha TCR chain-2A fusion, 2) beta TCR chain. SEQ ID No: 12 includes NheI and SalI restriction sites (underlined).

FIG. 5B is the amino acid sequence (SEQ ID No: 13) corresponding to FIG. 5A In FIG. 5B:

M1-S19 is a leader sequence which is removed on maturation of the wild type alpha chain TCR;

K20-S227 corresponds to the wild type alpha chain sequence SEQ ID No: 2;

K20-R254 corresponds to the wild type alpha chain extracellular domain;

I255-L271 is the alpha chain transmembrane region of the mature TCR;

W272-S274 is the alpha chain intracellular region of the mature TCR;

R277-R280 is the furin cleavage site to assist proteolytic removal, in the Golgi apparatus, of the P2A sequence A285-P303;

G275, S276, S281 to G284, R304 are flexible linkers allowing full function of the furin cleavage and P2A sequences;

M305-V323 is a leader sequence which is removed on maturation of the wild type beta chain TCR;

K324-D565 corresponds to the wild type beta chain sequence SEQ ID No: 3;

K324-E585 corresponds to the wild type beta chain extracellular domain;

I586-V607 is the beta chain transmembrane region of the mature TCR;

K608-G614 is the beta chain intracellular region of the mature TCR.

(d) T-Cells Transfected with Wild Type and High Affinity MAGE TCRs

Following the procedures described in (a) and (b) above, the MAGE-A3 alpha wt_2A_beta wt TCR gene (SEQ ID No: 12 (FIG. 5A)) was inserted into the pELNSxv lenti vector using the NheI and SalI restriction sites unique to both DNA constructs, and transfected T-cells created.

Similarly, T-cells may be created by transfection with genes identical to SEQ ID No: 12 (FIG. 5A) except that they encode (a) TCRs with the variable domain sequence (K1 to P114) of the wild type alpha chain SEQ ID No: 2, associated with a beta chain variable domain having one of SEQ ID Nos: 10 or 11; or (b) an alpha chain variable domain having one of SEQ ID Nos: 8 or 9 associated with the variable domain sequence (K1 to T112) of the wild type beta chain SEQ ID No: 3; or (c) an alpha chain variable domain having one of SEQ ID Nos: 8 or 9 associated with a beta chain variable domain having one of SEQ ID Nos: 10 or 11.

Example 6

Increased Activation of MAGE-A3 Improved-Affinity TCR-Transduced T Cells Compared to Wild Type-Affinity in Response to Tumour Cell Lines Elispot Protocol The following assay was carried out to demonstrate the activation of TCR-transduced cytotoxic T lymphocytes (CTLs) in response to tumour cell lines. IFN-γ production, as measured using the ELISPOT assay, was used as a read-out for cytotoxic T lymphocyte (CTL) activation.

Reagents

Assay media: 10% FCS (Gibco, Cat# 2011-09), 88% RPMI 1640 (Gibco, Cat# 42401), 1% glutamine (Gibco Cat# 25030) and 1% penicillin/streptomycin (Gibco Cat# 15070-063).

Wash buffer: 0.01M PBS/0.05% Tween 20

PBS (Gibco Cat# 10010)

The Human IFNγ ELISPOT PVDF-Enzymatic kit (Diaclone, France; Cat# 856.051.020) contains all other reagents required. (Capture and detection antibodies, skimmed milk powder, BSA, streptavidin-alkaline phosphatase and BCIP/NBT solution as well as the Human IFN-γ PVDF ELISPOT 96 well plates)

Method

Target Cell Preparation

The target cells used in this method were natural epitope-presenting cells: HCT-116 colorectal carcinoma and NCI-H1975 non-small cell lung carcinoma which are both HLA-$A1^+$ $MAGE^+$. N3 normal human epidermal melanocytes, which are HLA-$A1^+$ $MAGE^-$ were used as a negative control. Sufficient target cells (50,000 cells/well) were washed by centrifugation three times at 1200 rpm, 10 min in a Megafuge 1.0 (Heraeus). Cells were then re-suspended in assay media at $10^6$ cells/ml.

Effector Cell Preparation

The effector cells (T cells) used in this method were a 1:1 mix of CD4+ and CD8+ T cells (obtained by negative selection (using the CD4 and CD8 Negative Isolation Kits, Dynal) from PBL). Cells were stimulated with antiCD3/CD28 coated beads (T cell expander, Invitrogen), transduced with lentiviruses carrying the gene encoding the full αβ TCR of interest (based on the construct described in Example 5 and shown in FIG. 5B) and expanded in assay media containing 50 U/ml IL-2 until between 10 and 13 days post transduction. These cells were then placed in assay media prior to washing by centrifugation at 1200 rpm, 10 min in a Megafuge 1.0

(Heraeus). Cells were then re-suspended in assay media at a 4× the final required concentration.

ELISPOTs

Plates were prepared as follows: 100 μl anti-IFN-γ capture antibody was diluted in 10 ml sterile PBS per plate. 100 μl of the diluted capture antibody was then aliquoted into each well. The plates were then incubated overnight at 4° C. Following incubation the plates were washed (programme 1, plate type 2, Ultrawash Plus 96-well plate washer; Dynex) to remove the capture antibody. Plates were then blocked by adding 100 μl 2% skimmed milk in sterile PBS to each well and incubating the plates at room temperature for two hours. The skimmed milk was then washed from the plates (programme 1, plate type 2, Ultrawash Plus 96-well plate washer, Dynex) and any remaining wash buffer was removed by flicking and tapping the ELISPOT plates on a paper towel.

The constituents of the assay were then added to the ELISPOT plate in the following order:

50 μl of target cells $10^6$ cells/ml (giving a total of 50,000 target cells/well). Media sufficient to give 200 ul per well final volume (assay media).

50 μl effector cells (5,000 mixed transduced CD4/8$^+$ cells/well).

The plates were then incubated overnight (37° C./5% $CO_2$). The next day the plates were washed three times (programme 1, plate type 2, Ultrawash Plus 96-well plate washer, Dynex) with wash buffer and tapped on paper towel to remove excess wash buffer. 100 μl primary detection antibody was then added to each well. The primary detection antibody was prepared by adding 550 μl of distilled water to a vial of detection antibody supplied with the Diaclone kit. 100 μl of this solution was then diluted in 10 ml PBS/1% BSA (the volume required for a single plate). Plates were then incubated at room temperature for at least 2 hr prior to being washed three times (programme 1, plate type 2, Ultrawash Plus 96-well plate washer, Dynex) with wash buffer, excess wash buffer was removed by tapping the plate on a paper towel.

Secondary detection was performed by adding 100 μl of diluted streptavidin-Alkaline phosphatase to each well and incubating the plate at room temperature for 1 hour. The streptavidin-Alkaline phosphatase was prepared by addition of 10 μl streptavidin-Alkaline phosphatase to 10 ml PBS/1% BSA (the volume required for a single plate). The plates were then washed three times (programme 1, plate type 2, Ultrawash Plus 96-well plate washer, Dynex) with wash buffer and tapped on paper towel to remove excess wash buffer. 100 μl of BCIP/NBT solution, as supplied with the Diaclone kit, was then added to each well. During development plates were covered in foil and left for 5-15 min. Developing plates were regularly checked for spots during this period to determine optimal time to terminate the reaction. The plates were washed in a sink full of tap water to terminate the development reaction, and shaken dry prior to their disassembly into their three constituent parts. The plates were then dried at 50° C. for 1 hr prior to counting the spots that have formed on the membrane using an Immunospot Plate reader (CTL; Cellular Technology Limited).

Results

IFNγ release by activated TCR-transduced T cells in response to a variety of MAGE-A3-positive and control tumour cell lines was tested by ELISPOT assay (as described above). The number of ELISPOT spots observed in each well was plotted using Prism (Graph Pad).

CD4$^+$, CD8$^+$or mixed CD4$^+$/CD8$^+$T cells expressing a) TCR No:1, b) TCR No:2, c) TCR No:3, d) TCR No:4 or e) TCR No:5 (as described in the table below) were incubated with MAGE-A3$^+$ HLA:A1$^+$ tumour cell lines HCT-116 or NCI-H1975 or with MAGE-A3$^-$ HLA:A1$^+$ N3 melanocytes. Non-transduced T cells (Nt) were also used as a negative control.

| TCR No | TCR α variable domain SEQ ID NO: | TCR β variable domain SEQ ID NO: |
|---|---|---|
| 1 | K1 to P114 of SEQ ID No: 2 | K1 to T112 of SEQ ID No: 3 |
| 2 | 9 | K1 to T112 of SEQ ID No: 3 |
| 3 | 8 | K1 to T112 of SEQ ID No: 3 |
| 4 | K1 to P114 of SEQ ID No: 2 | 10 |
| 5 | K1 to P114 of SEQ ID No: 2 | 11 |

FIG. 6 demonstrates that TCR No:1-transduced T cells did not release IFNγ in response to tumour cell lines. TCR No: 2-transduced T cells released IFNγ in response to HCT-116 colorectal carcinoma cells only.

Improved-affinity MAGE-A3 TCR No: 3-, 4- and 5-transduced T cells responded in greater numbers to HCT-116 cells but also responded to NCI-H1975 cells.

Example 7

Increased Cytotoxicity of MAGE-A3 Improved-Affinity TCR-Transduced T Cells in Response to a Tumour Cell Line than Wild Type This assay is a colorimetric alternative to $^{51}Cr$ release radioactive cytotoxicity assays and quantitatively measures lactate dehydrogenase (LDH) which is an enzyme that is released upon cell lysis. Released LDH in culture supernatants is measured with a 30-minute coupled enzymatic assay, which results in the conversion of a tetrazolium salt (INT) into a red formazan product. The amount of colour formed is proportional to the number of lysed cells. The absorbance data is collected using a standard 96-well plate reader at 490 nm.

Materials

- CytoTox96® Non-Radioactive Cytotoxicity Assay (Promega) (G1780) contains Substrate Mix, Assay Buffer, Lysis Solution, and Stop Solution
- Culture media: 10% FCS (heat-inactivated, Gibco, cat# 10108-165), 88% RPMI 1640 with phenol red (Invitrogen, cat# 42401042), 1% glutamine, 200 mM (Invitrogen, cat# 25030024), 1% penicillin/streptomycin (Invitrogen cat# 15070063)
- Assay media: 10% FCS (heat-inactivated, Gibco, cat# 10108-165), 88% RPMI 1640 without phenol red (Invitrogen, cat# 32404014), 1% glutamine, 200 mM (Invitrogen, cat# 25030024), 1% penicillin/streptomycin (Invitrogen cat# 15070063)
- Nunc microwell round bottom 96 well tissue culture plate (Nunc, cat# 163320)
- Nunc-Immuno plates Maxisorb (Nunc, cat# 442404)

Method

Target Cell Preparation

The targets cells (T) used in this assay were the HCT-116 colorectal carcinoma cell line (HLA-A1$^+$ MAGE-A3$^+$) with or without knockdown of MAGE-A3/6 protein expression by shRNA (knockdown performed as described below). Target cells were prepared in assay medium: target cell concentration was adjusted to $2\times10^5$ cells/ml to give $1\times10^4$ cells/well in 50 μl.

MAGE-A3/6 Knockdown by siRNA

HCT-116 cells were transduced with lentiviral particles encoding MAGE-A3/6 shRNA (Santi Cruz Biotech, cat# sc-45284-V) as described in the manufacturers' instructions.

Briefly, $4\times10^4$ cells were plated per well of a 96 well flat bottom tissue culture plate (100 µl/well) and incubated overnight to adhere. Roughly 50% confluency was aimed for. The following day 10 µl medium was replaced with 10 µl of 100 µg/ml polybrene (diluted in culture medium; Santa Cruz Biotech, cat# sc-134220) to give 5 µg/ml final concentration per well. The shRNA lentiviral particle-containing supernatant was defrosted slowly at room temperature and mixed gently. 60 µl of lentiviral particle-containing supernatant was then added per well with a further 40 µl culture medium to give 200 µl total volume per well, and cells incubated overnight. After 18 h medium was gently removed and replaced with 200 µl of fresh culture medium without polybrene. The next day cells were detached with 0.25% Trypsin-EDTA (Invitrogen, cat# 25200) and seeded into 6 well plates for expansion in fresh medium containing 5 µg/ml puromycin hydrochloride (Santa Cruz Biotech, cat# sc-108071) for selection of shRNA-expressing cells. Cells were frozen after several rounds of expansion. MAGE-A3/6 protein expression knockdown was assessed by Western blot.

Effector Cell Preparation

The effector cells (E) used in this assay were mixed $CD8^+$ and $CD4^+$ T cells (1:1) stimulated, transduced and expanded as described previously (Example 7). The effector to target ratio was 1.25:1. Effector cells were prepared in assay medium; cell concentration was adjusted to $2.5\times10^5$/ml to give $1.25\times10^5$ in 50 µl.

Assay Preparation

The constituents of the assay were added to the plate in the following order:

- assay medium (to give 150 µl total per well)
- 50 µl of target cells (prepared as explained previously) to each well
- 50 µl of effector cells (prepared as explained previously) to each well Several controls were prepared as explained below:

- Effector spontaneous release: 50 µl effector cells alone.
- Target cells spontaneous release: 50 µl target cells alone.
- Target maximum release: 50 µl target cells alone+10 µl of digitonin (600 µg/ml to give 40 µg/ml final)
- Assay medium control: 150 µl medium alone.
- Assay medium volume control for lysis solution: 150 µl medium+10 µl of digitonin.

All wells are prepared in triplicate in a final volume of 150 µl.

The plate was centrifuged at 250×g for 4 minutes then incubated at 37° C. for 24 hours. The plate was centrifuged at 250×g for 4 minutes. 50 µl of the supernatant from each well of the assay plate was transferred to the corresponding well of a flat-bottom 96 well Nunc Maxisorb plate. The Substrate Mix was reconstituted using Assay Buffer (12 ml). 50 µl of the reconstituted Substrate Mix was then added to each well of the plate. The plate was covered with aluminium foil and incubated at room temperature for 30 minutes. 50 µl of Stop Solution was added to each well of the plate to stop the reaction. The absorbance at 490 nm was recorded on an ELISA plate reader within one hour after the addition of Stop Solution.

Calculation of Results

The average of absorbance values of the Culture Medium Background was subtracted from all absorbance values of Experimental, Target Cell Spontaneous Release and Effector Cell Spontaneous Release.

The average of the absorbance values of the Volume Correction Control was subtracted from the absorbance values obtained for the Target Cell Maximum Release Control.

The corrected values obtained in the first two steps were used in the following formula to compute percent cytotoxicity:

% cytotoxicity=100×(Experimental−Effector Spontaneous−Target Spontaneous)/(Target Maximum−Target Spontaneous)

Results

Figure 7:
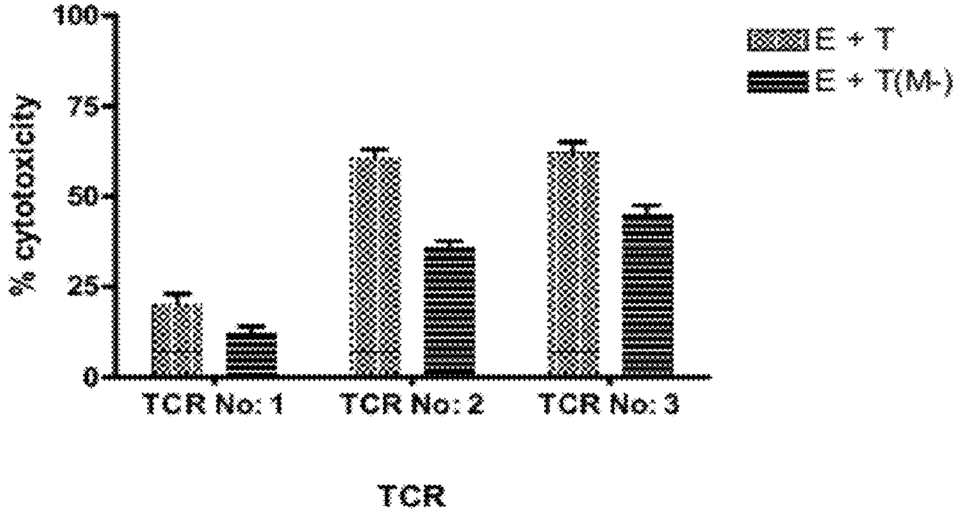
FIG. 7 shows a cytotoxicity assay where killing of tumour cell lines by MAGE-A3-transduced T-cells is tested.

The graph in FIG. 7 shows the specific killing of colorectal carcinoma cells by T cells transduced to express TCR No:1, TCR No:2 or TCR No:3 (as described in the table below). The TCR No:2-transduced T cells and TCR No:3-transduced T cells kill MAGE-A3-expressing HCT-116 colorectal carcinoma cells, with an increased cytotoxicity compared to the wild-type TCR No:1-transduced T cells. This killing is reduced by shRNA knockdown of MAGE-A3/6 protein expression in the HCT-116 cells (T(M-)).

| TCR No | TCR α variable domain SEQ ID NO: | TCR β variable domain SEQ ID NO: |
|---|---|---|
| 1 | K1 to P114 of SEQ ID No: 2 | K1 to T112 of SEQ ID No: 3 |
| 2 | 8 | K1 to T112 of SEQ ID No: 3 |
| 3 | K1 to P114 of SEQ ID No: 2 | 10 |

The invention claimed is:

1. A T cell receptor (TCR) having the property of binding to SEQ ID NO: 1-Human Leukocyte Antigen (HLA)-A1 complex and comprising a TCR α variable domain and a TCR β variable domain, wherein:

the TCR α variable domain has the amino acid sequence from K1 to P114 of SEQ ID NO: 2 and the TCR β variable domain has the amino acid sequence from K1 to T112 of SEQ ID NO: 3 except that, in the TCR a variable domain, at least one of the following mutations is present:

50I is mutated to 50V;

51Q is mutated to 51R;

52S is mutated to 52P;

53S is mutated to 53Y; and/or in the TCR beta variable domain, at least one of the following mutations is present:

50F is mutated to 50T;

51S is mutated to 51D;

52E is mutated to 52M;

53T is mutated to 53L;

54Q is mutated to 54L.

2. A TCR as claimed in claim 1 comprising one of the α chain variable domain amino acid sequences SEQ ID NOs: 8 and 9.

3. A TCR as claimed in claim 1 comprising one of the β chain variable domain amino acid sequences SEQ ID NOs: 10 and 11.

4. A TCR as claimed in claim 1, also having α chain TCR alpha constant(TRAC) constant domain and a β chain TCR beta constant(TRBC)1 or TRBC2 constant domain, or having an α chain TRAC and β chain TRBC1 or TRBC2 constant domains modified by truncation or substitution to delete the native disulfide bond between Cys4 of exon 2 of TRAC and Cys2 of exon 2 of TRBC1.

5. A TCR as claimed in claim 1 which is an αβ heterodimeric TCR, and which has α and β chain constant domain sequences in which cysteine residues are substituted for Thr 48 of T-cell receptor alpha constant (TRAC) and Ser 57 of TRBC1 or TRBC2, the said cysteines forming a disulfide bond between the α and β constant domains of the TCR.

* * * * *

SEQUENCE LISTING

```
<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Glu Val Asp Pro Ile Gly His Leu Tyr
1               5


<210> SEQ ID NO 2
<211> LENGTH: 208
<212> TYPE: PRT
<213> ORGANISM: Homo sapiens

<400> SEQUENCE: 2
```

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Gly Gly
                85                  90                  95

Ala Gly Ser Tyr Gln Leu Thr Phe Gly Lys Gly Thr Lys Leu Ser Val
            100                 105                 110

Ile Pro Asn Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205


<210> SEQ ID NO 3
<211> LENGTH: 242
<212> TYPE: PRT
<213> ORGANISM: Homo sapiens

<400> SEQUENCE: 3

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Pro Asn
                85                  90                  95

Met Ala Asp Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175
```

```
Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp


<210> SEQ ID NO 4
<211> LENGTH: 637
<212> TYPE: DNA
<213> ORGANISM: Homo sapiens

<400> SEQUENCE: 4

catatgaaac aagaagttac tcaaattcct gcagctctga gtgtcccaga aggagaaaac     60

ttggttctca actgcagttt cactgatagc gctatttaca acctccagtg gtttaggcag    120

gaccctggga aaggtctcac atctctgttg cttattcagt caagtcagag agagcaaaca    180

agtggaagac ttaatgcctc gctggataaa tcatcaggac gtagtacttt atacattgca    240

gcttctcagc ctggtgactc agccacctac ctctgtgctg tgaggccggg aggggctggg    300

agttaccaac tcactttcgg gaaggggacc aaactctcgg tcataccaaa tatccagaac    360

cctgaccctg ccgtgtacca gctgagagac tctaagtcga gtgacaagtc tgtctgccta    420

ttcaccgatt ttgattctca aacaaatgtg tcacaaagta aggattctga tgtgtatatc    480

acagacaaat gtgtgctaga catgaggtct atggacttca agagcaacag tgctgtggcc    540

tggagcaaca aatctgactt tgcatgtgca aacgccttca acaacagcat tattccagaa    600

gacaccttct tccccagccc agaaagttcc taagctt                             637


<210> SEQ ID NO 5
<211> LENGTH: 739
<212> TYPE: DNA
<213> ORGANISM: Homo sapiens

<400> SEQUENCE: 5

catatgaaag ctggagttac tcaaactcca agatatctga tcaaaacgag aggacagcaa     60

gtgacactga gctgctcccc tatctctggg cataggagtg tatcctggta ccaacagacc    120

ccaggacagg gccttcagtt cctctttgaa tacttcagtg agacacagag aaacaaagga    180

aacttccctg gtcgattctc agggcgccag ttctctaact ctcgctctga gatgaatgtg    240

agcaccttgg agctgggga ctcggccctt tatctttgcg ccagcagccc gaacatggcc    300

gacgagcagt acttcgggcc gggcaccagg ctcacggtca cagaggacct gaaaaacgtg    360

ttcccacccg aggtcgctgt gtttgagcca tcagaagcag agatctccca cacccaaaag    420

gccacactgg tgtgcctggc caccggtttc taccccgacc acgtggagct gagctggtgg    480

gtgaatggga aggaggtgca cagtggggtc tgcacagacc cgcagcccct caaggagcag    540

cccgccctca atgactccag atacgctctg agcagccgcc tgagggtctc ggccaccttc    600

tggcaggacc cccgcaacca cttccgctgt caagtccagt tctacgggct ctcggagaat    660

gacgagtgga cccaggatag ggccaaaccc gtcacccaga tcgtcagcgc cgaggcctgg    720

ggtagagcag actaagctt                                                 739
```

-continued

<210> SEQ ID NO 6
<211> LENGTH: 208
<212> TYPE: PRT
<213> ORGANISM: Artificial Sequence
<220> FEATURE:
<223> OTHER INFORMATION: Wild type MAGE TCR apha chin with introduced cysteine

<400> SEQUENCE: 6

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Gly Gly
                85                  90                  95

Ala Gly Ser Tyr Gln Leu Thr Phe Gly Lys Gly Thr Lys Leu Ser Val
            100                 105                 110

Ile Pro Asn Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205
```

<210> SEQ ID NO 7
<211> LENGTH: 242
<212> TYPE: PRT
<213> ORGANISM: Artificial Sequence
<220> FEATURE:
<223> OTHER INFORMATION: WT MAGE TCR Beta Chain with introduced cysteine and other modifications

<400> SEQUENCE: 7

```
Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Pro Asn
                85                  90                  95

Met Ala Asp Glu Gln Tyr Phe Gly Pro Gly Thr Arg Leu Thr Val Thr
            100                 105                 110
```

Glu Asp Leu Lys Asn Val Phe Pro Pro Glu Val Ala Val Phe Glu Pro
115 120 125

Ser Glu Ala Glu Ile Ser His Thr Gln Lys Ala Thr Leu Val Cys Leu
130 135 140

Ala Thr Gly Phe Tyr Pro Asp His Val Glu Leu Ser Trp Trp Val Asn
145 150 155 160

Gly Lys Glu Val His Ser Gly Val Cys Thr Asp Pro Gln Pro Leu Lys
165 170 175

Glu Gln Pro Ala Leu Asn Asp Ser Arg Tyr Ala Leu Ser Ser Arg Leu
180 185 190

Arg Val Ser Ala Thr Phe Trp Gln Asp Pro Arg Asn His Phe Arg Cys
195 200 205

Gln Val Gln Phe Tyr Gly Leu Ser Glu Asn Asp Glu Trp Thr Gln Asp
210 215 220

Arg Ala Lys Pro Val Thr Gln Ile Val Ser Ala Glu Ala Trp Gly Arg
225 230 235 240

Ala Asp

<210> SEQ ID NO 8
<211> LENGTH: 114
<212> TYPE: PRT
<213> ORGANISM: Artificial Sequence
<220> FEATURE:
<223> OTHER INFORMATION: High Affinity MAGE Alpha Chain Variable Domain

<400> SEQUENCE: 8

Lys Gln Glu Val Thr Gln Ile Pro Ala Ala Leu Ser Val Pro Glu Gly
1 5 10 15

Glu Asn Leu Val Leu Asn Cys Ser Phe Thr Asp Ser Ala Ile Tyr Asn
20 25 30

Leu Gln Trp Phe Arg Gln Asp Pro Gly Lys Gly Leu Thr Ser Leu Leu
35 40 45

Leu Val Arg Pro Tyr Gln Arg Glu Gln Thr Ser Gly Arg Leu Asn Ala
50 55 60

Ser Leu Asp Lys Ser Ser Gly Arg Ser Thr Leu Tyr Ile Ala Ala Ser
65 70 75 80

Gln Pro Gly Asp Ser Ala Thr Tyr Leu Cys Ala Val Arg Pro Gly Gly
85 90 95

Ala Gly Ser Tyr Gln Leu Thr Phe Gly Lys Gly Thr Lys Leu Ser Val
100 105 110

Ile Pro

<210> SEQ ID NO 9
<211> LENGTH: 114
<212> TYPE: PRT
<213> ORGANISM: Artificial Sequence
<220> FEATURE:
<223> OTHER INFORMATION: High Affinity MAGE TCR Alpha Chain Variable Domain

<400> SEQUENCE: 9

Lys Gln Glu Val Thr Gln Ile Pro Ala Ala Leu Ser Val Pro Glu Gly
1 5 10 15

Glu Asn Leu Val Leu Asn Cys Ser Phe Thr Asp Ser Ala Ile Tyr Asn
20 25 30

Leu Gln Trp Phe Arg Gln Asp Pro Gly Lys Gly Leu Thr Ser Leu Leu
35 40 45

```
Leu Val Arg Pro Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Gly Gly
                85                  90                  95

Ala Gly Ser Tyr Gln Leu Thr Phe Gly Lys Gly Thr Lys Leu Ser Val
            100                 105                 110

Ile Pro


<210> SEQ ID NO 10
<211> LENGTH: 112
<212> TYPE: PRT
<213> ORGANISM: Artificial Sequence
<220> FEATURE:
<223> OTHER INFORMATION: High Affinity MAGE Beta Chain Variable Domain

<400> SEQUENCE: 10

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Thr Asp Met Thr Leu Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Pro Asn
                85                  90                  95

Met Ala Asp Glu Gln Tyr Phe Gly Pro Gly Thr Arg Leu Thr Val Thr
            100                 105                 110


<210> SEQ ID NO 11
<211> LENGTH: 112
<212> TYPE: PRT
<213> ORGANISM: Artificial Sequence
<220> FEATURE:
<223> OTHER INFORMATION: High Affinity MAGE TCR Beta Chain Variable
      Domain

<400> SEQUENCE: 11

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Asp Met Leu Leu Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Pro Asn
                85                  90                  95

Met Ala Asp Glu Gln Tyr Phe Gly Pro Gly Thr Arg Leu Thr Val Thr
            100                 105                 110


<210> SEQ ID NO 12
<211> LENGTH: 1864
```

-continued

<212> TYPE: DNA
<213> ORGANISM: Artificial Sequence
<220> FEATURE:
<223> OTHER INFORMATION: WT MAGE TCR alpha and beta chains with porcine
teschovirus-1 2A Sequence insertion

<400> SEQUENCE: 12

```
gctagccgcc accatggaaa ccctgctggg cctgctgatc ctgtggctgc agctgcagtg     60

ggtctcttcg aagcaggaag tgacccagat ccctgccgcc ctgagcgtgc ccgagggcga    120

gaacctggtg ctgaactgca gcttcaccga cagcgccatc tacaacctgc agtggttccg    180

gcaggacccc ggcaagggcc tgaccagcct gctgctgatc cagagcagcc agcgggagca    240

gaccagcggc agactgaacg ccagcctgga caagagcagc ggcagaagca ccctgtatat    300

cgccgccagc cagcccggcg actccgccac ctacctgtgc gctgtgcggc ctggcggagc    360

cggcagctac cagctgacct tcggcaaggg caccaagctg tccgtgatcc ccaatattca    420

gaaccccgac cccgccgtgt accagctgcg ggacagcaag tccagcgaca agagcgtgtg    480

cctgttcacc gacttcgaca gccagaccaa cgtgtcccag agcaaggaca gcgacgtgta    540

catcaccgac aagaccgtgc tggacatgcg gagcatggac ttcaagagca acagcgccgt    600

ggcctggtcc aacaagagcg acttcgcctg cgccaacgcc ttcaacaaca gcatcatccc    660

cgaggacacc tttttcccca gccccgagag cagctgcgac gtcaaactgg tggagaagtc    720

cttcgagaca gacaccaacc tgaacttcca gaacctgagc gtgatcggct tcagaattct    780

gctgctgaag gtggccggct tcaacctgct gatgaccctg cggctgtgga gcagcggctc    840

ccgggccaag agaagcggat ccggcgccac caacttttcc ctgctgaagc aggctggaga    900

tgtggaggaa aaccctggcc ctaggatggg cagcagactg ctgtgctggg tgctgctgtg    960

tctgctggga gccggccctg tgaaggccgg cgtgacccag acccccagat acctgatcaa   1020

gaccagaggc cagcaggtga cactgagctg cagccccatc agcggccaca gaagcgtgtc   1080

ctggtatcag cagacccccg gacagggcct gcagttcctg ttcgagtact tcagcgagac   1140

acagcggaac aagggcaact tccccggcag attcagcggc aggcagttca gcaacagccg   1200

cagcgagatg aacgtgtcca ccctggaact gggcgacagc gccctgtacc tgtgtgccag   1260

cagccccaac atggccgacg agcagtactt cggccctggc acccggctga cggtaaccga   1320

ggacctgaag aacgtgttcc cccccgaggt ggccgtgttc gagcccagcg aggccgagat   1380

cagccacacc cagaaagcca ccctggtgtg cctggccacc ggcttctacc ccgaccacgt   1440

ggagctgtct tggtgggtga acggcaaaga ggtgcacagc ggagtctcca ccgaccccca   1500

gcccctgaaa gagcagcccg ccctgaacga cagccggtac tgcctgagca gcagactgcg   1560

ggtgtccgcc accttctggc agaaccctag aaaccacttc cggtgccagg tgcagttcta   1620

cggcctgagc gagaacgacg agtggaccca ggacagagcc aagcccgtga cacagatcgt   1680

gtccgccgag gcctgggggc gcgccgattg cggcttcaca agcgagagct atcagcaggg   1740

cgtgctgtct gccaccatcc tgtacgagat cctgctgggc aaggccaccc tgtacgccgt   1800

gctggtgtcc gccctggtgc tgatggccat ggtgaagcgg aaggacagcc ggggctaagt   1860

cgac                                                                1864
```

<210> SEQ ID NO 13
<211> LENGTH: 614
<212> TYPE: PRT
<213> ORGANISM: Artificial Sequence
<220> FEATURE:
<223> OTHER INFORMATION: WT Mage TCR alpha and beta chains with porcine
teschovirus-1 2A insertion

<400> SEQUENCE: 13

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Gly Gly Ala Gly Ser Tyr Gln Leu Thr Phe Gly Lys Gly Thr Lys
        115                 120                 125

Leu Ser Val Ile Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser Gly Ser Arg Ala Lys Arg Ser Gly Ser Gly Ala Thr Asn Phe
        275                 280                 285

Ser Leu Leu Lys Gln Ala Gly Asp Val Glu Glu Asn Pro Gly Pro Arg
    290                 295                 300

Met Gly Ser Arg Leu Leu Cys Trp Val Leu Leu Cys Leu Leu Gly Ala
305                 310                 315                 320

Gly Pro Val Lys Ala Gly Val Thr Gln Thr Pro Arg Tyr Leu Ile Lys
                325                 330                 335

Thr Arg Gly Gln Gln Val Thr Leu Ser Cys Ser Pro Ile Ser Gly His
            340                 345                 350

Arg Ser Val Ser Trp Tyr Gln Gln Thr Pro Gly Gln Gly Leu Gln Phe
        355                 360                 365

Leu Phe Glu Tyr Phe Ser Glu Thr Gln Arg Asn Lys Gly Asn Phe Pro
    370                 375                 380

Gly Arg Phe Ser Gly Arg Gln Phe Ser Asn Ser Arg Ser Glu Met Asn
385                 390                 395                 400

Val Ser Thr Leu Glu Leu Gly Asp Ser Ala Leu Tyr Leu Cys Ala Ser
                405                 410                 415
```

-continued

```
Ser Pro Asn Met Ala Asp Glu Gln Tyr Phe Gly Pro Gly Thr Arg Leu
            420                 425                 430

Thr Val Thr Glu Asp Leu Lys Asn Val Phe Pro Pro Glu Val Ala Val
        435                 440                 445

Phe Glu Pro Ser Glu Ala Glu Ile Ser His Thr Gln Lys Ala Thr Leu
    450                 455                 460

Val Cys Leu Ala Thr Gly Phe Tyr Pro Asp His Val Glu Leu Ser Trp
465                 470                 475                 480

Trp Val Asn Gly Lys Glu Val His Ser Gly Val Ser Thr Asp Pro Gln
                485                 490                 495

Pro Leu Lys Glu Gln Pro Ala Leu Asn Asp Ser Arg Tyr Cys Leu Ser
            500                 505                 510

Ser Arg Leu Arg Val Ser Ala Thr Phe Trp Gln Asn Pro Arg Asn His
        515                 520                 525

Phe Arg Cys Gln Val Gln Phe Tyr Gly Leu Ser Glu Asn Asp Glu Trp
    530                 535                 540

Thr Gln Asp Arg Ala Lys Pro Val Thr Gln Ile Val Ser Ala Glu Ala
545                 550                 555                 560

Trp Gly Arg Ala Asp Cys Gly Phe Thr Ser Glu Ser Tyr Gln Gln Gly
                565                 570                 575

Val Leu Ser Ala Thr Ile Leu Tyr Glu Ile Leu Leu Gly Lys Ala Thr
            580                 585                 590

Leu Tyr Ala Val Leu Val Ser Ala Leu Val Leu Met Ala Met Val Lys
        595                 600                 605

Arg Lys Asp Ser Arg Gly
    610


<210> SEQ ID NO 14
<211> LENGTH: 36
<212> TYPE: DNA
<213> ORGANISM: Artificial Sequence
<220> FEATURE:
<223> OTHER INFORMATION: Restriction site oligineucleotide

<400> SEQUENCE: 14

ggaattccat atgaaacaag aagttactca aattcc                              36


<210> SEQ ID NO 15
<211> LENGTH: 36
<212> TYPE: DNA
<213> ORGANISM: Artificial Sequence
<220> FEATURE:
<223> OTHER INFORMATION: Restriction site oligonucleotide

<400> SEQUENCE: 15

ttgtcagtcg acttagagtc tctcagctgg tacacg                              36


<210> SEQ ID NO 16
<211> LENGTH: 38
<212> TYPE: DNA
<213> ORGANISM: Artificial Sequence
<220> FEATURE:
<223> OTHER INFORMATION: Restriction site oligonucleotide

<400> SEQUENCE: 16

gaattccata tgaaagctgg agttactcaa actccaag                            38


<210> SEQ ID NO 17
<211> LENGTH: 32
<212> TYPE: DNA
```

-continued

```
<213> ORGANISM: Artificial Sequence
<220> FEATURE:
<223> OTHER INFORMATION: Restriction site oligonucleotide

<400> SEQUENCE: 17

tagaaaccgg tggccaggca caccagtgtg gc                              32


<210> SEQ ID NO 18
<211> LENGTH: 9
<212> TYPE: PRT
<213> ORGANISM: Homo sapiens

<400> SEQUENCE: 18

Lys Ile Phe Gly Ser Leu Ala Phe Leu
1               5
```